United States Patent [19]

Beck et al.

[11] 4,418,566
[45] Dec. 6, 1983

[54] GAS ANALYZING TECHNIQUES

[75] Inventors: James E. Beck, Des Plaines; Arvind M. Patel, Chicago, both of Ill.

[73] Assignee: Sun Electric Corporation, Crystal Lake, Ill.

[21] Appl. No.: 342,606

[22] Filed: Jan. 25, 1982

[51] Int. Cl.³ ............................................. G01N 27/00
[52] U.S. Cl. ......................................... 73/23; 364/828
[58] Field of Search ................... 73/23; 364/163, 828; 123/440, 489; 60/276, 285

[56] References Cited

U.S. PATENT DOCUMENTS

| 3,333,185 | 7/1967 | Riseman et al. | 364/828 |
| 4,030,349 | 6/1977 | Blanke et al. | 73/23 |
| 4,031,747 | 6/1977 | Blanke | 73/23 |

Primary Examiner—Stephen A. Kreitman
Attorney, Agent, or Firm—Allegretti, Newitt, Witcoff & McAndrews, Ltd.

[57] ABSTRACT

Gas analyzing techniques for monitoring the amount of oxygen in the exhaust of motor vehicles. An oxygen sensor produces a sensor signal having a sensor value proportional to the partial pressure of the oxygen produced by the motor vehicle. Processing circuitry generates a resulting signal proportional to the sum of the sensor value, another value proportional to the first derivative of the sensor value and a third value proportional to the second derivative of the sensor value. The resulting signal can be used to predict the final sensor value at a point in time earlier than would be otherwise possible.

6 Claims, 4 Drawing Figures

GAS ANALYZING TECHNIQUES

BACKGROUND AND SUMMARY

Apparatus for analyzing various gases in the exhaust of motor vehicles has been in use for a number of years. Typically, such apparatus includes sensors for detecting the amount of hydrocarbons (HC) and carbon monoxide (CO) in the exhaust. The sensors convert the concentration of the gases into a corresponding electrical signal which is processed by electronic circuitry and displayed either on a CRT screen or a meter.

More recently, it has been found advantageous to include in such apparatus the ability to detect the amount of oxygen ($O_2$) in the vehicle exhaust. Unfortunately, commercial oxygen sensors are much slower acting than corresponding commercial HC or CO sensors. While a display of HC or CO concentration can generally be obtained in approximately 8 seconds, it frequently takes 16 seconds or longer for the oxygen sensor and its related circuitry to create a display of the concentration of oxygen. The delay in creating the oxygen display is confusing to the operator of the apparatus, especially when he receives the display of the HC and CO concentrations at an earlier time.

There have been attempts in the past to speed up the display of oxygen concentration in gas analyzing apparatus. For example, in U.S. Pat. No. 4,030,349 (Blanke et al.—June 21, 1977), the first derivative of the oxygen signal is displayed in order to obtain an advanced indication of the value of the oxygen signal itself. Although this approach may be a step in the right direction, it still does not provide an adequate display of the concentration of $O_2$ within the same time period as the corresponding HC or CO displays.

In order to provide an improved analyzer, the applicants have taken an entirely new approach. They generate a resulting signal proportional to the sum of: (1) a first value proportioned to the oxygen sensor output, (2) a second value proportional to the first derivative of the oxygen sensor output and (3) a third value proportional to the second derivative of the oxygen sensor output. They have surprisingly discovered that by summing these three types of values, they can accurately predict the concentration of oxygen in the exhaust of a vehicle at a much earlier time than previously has been possible.

Accordingly, it is principal object of the invention to provide improved apparatus for anticipating or predicting the concentration of a gas, such as oxygen, at a rapid rate.

Another object of the invention is to provide apparatus of the foregoing type in which values of the oxygen signal and derivatives thereof are summed by electrical circuitry.

Another object of the invention is to provide apparatus of the foregoing type in which a three pole filter is utilized in order to more accurately predict the concentration of the gas.

DESCRIPTION OF THE DRAWINGS

These and other objects, advantages and features of the present invention will hereinafter appear for purposes of illustration, but not of limitation, in connection with the accompanying drawings wherein.

DESCRIPTION OF THE PREFERRED EMBODIMENT

Figure 1:
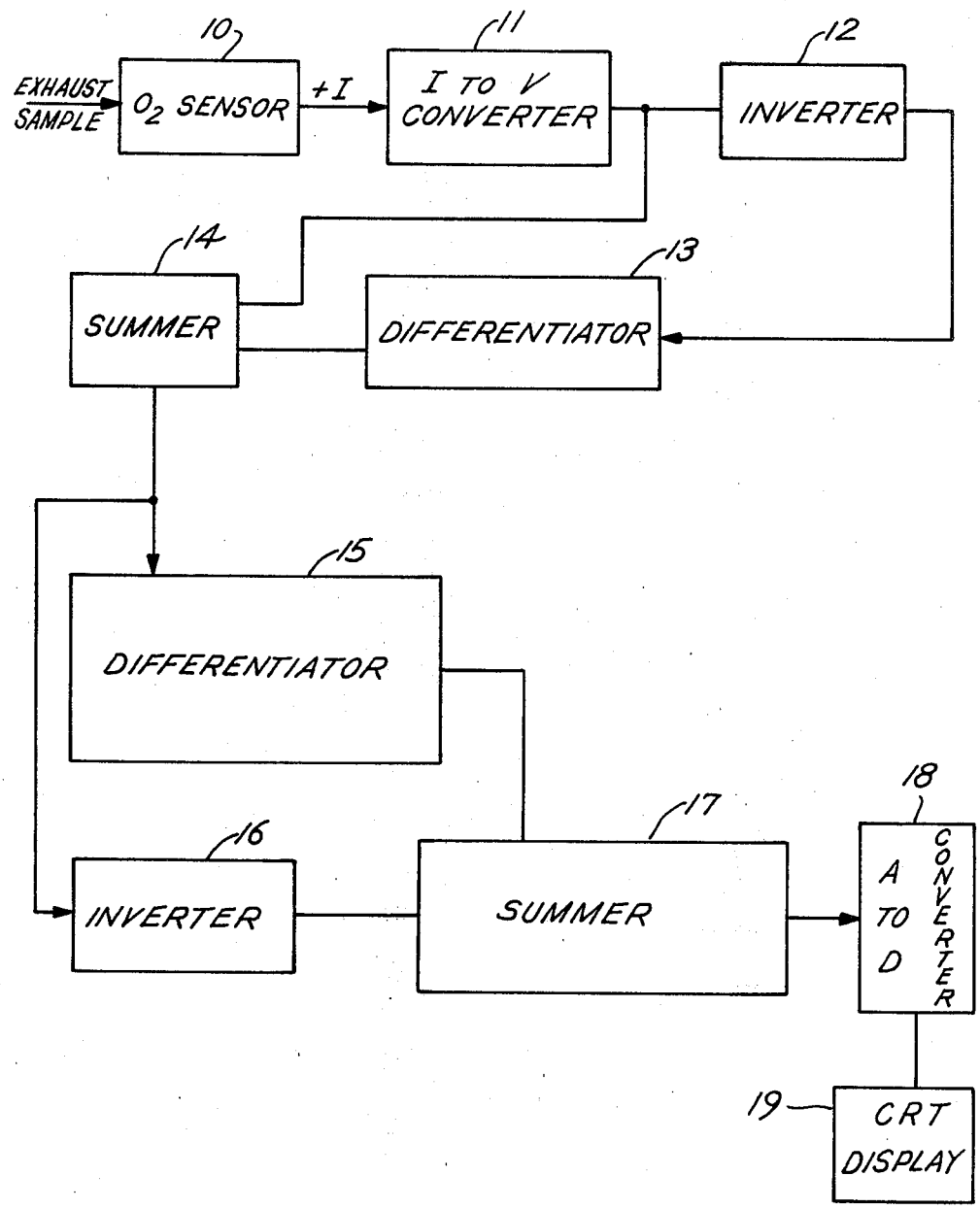
FIG. 1 is an electrical schematic block diagram of a preferred form of apparatus made in accordance with the present invention.

Referring to FIG. 1, the invention, in its preferred form, is intended for use in connection with a conventional oxygen sensor 10 which is commercially available. One such oxygen sensor is described in detail in the above-identified Blanke patent.

A preferred form of circuitry embodying the present invention basically comprises a current to voltage converter 11, and inverter 12, a summer 14 which algebraically adds the signals from converter 11 and a differentiator 13, another differentiator circuit 15, an inverter 16 and a final summer circuit 17 which algebraically adds the values from differentiator 15 and inverter 16. In the preferred embodiment, the output of summer 17 is transmitted to an analog to digital converter 18 and thereafter is displayed on a CRT screen 19 for use by an operator who is attempting to adjust an engine by use of the concentration of oxygen in the exhaust stream created by the engine.

Figure 2:
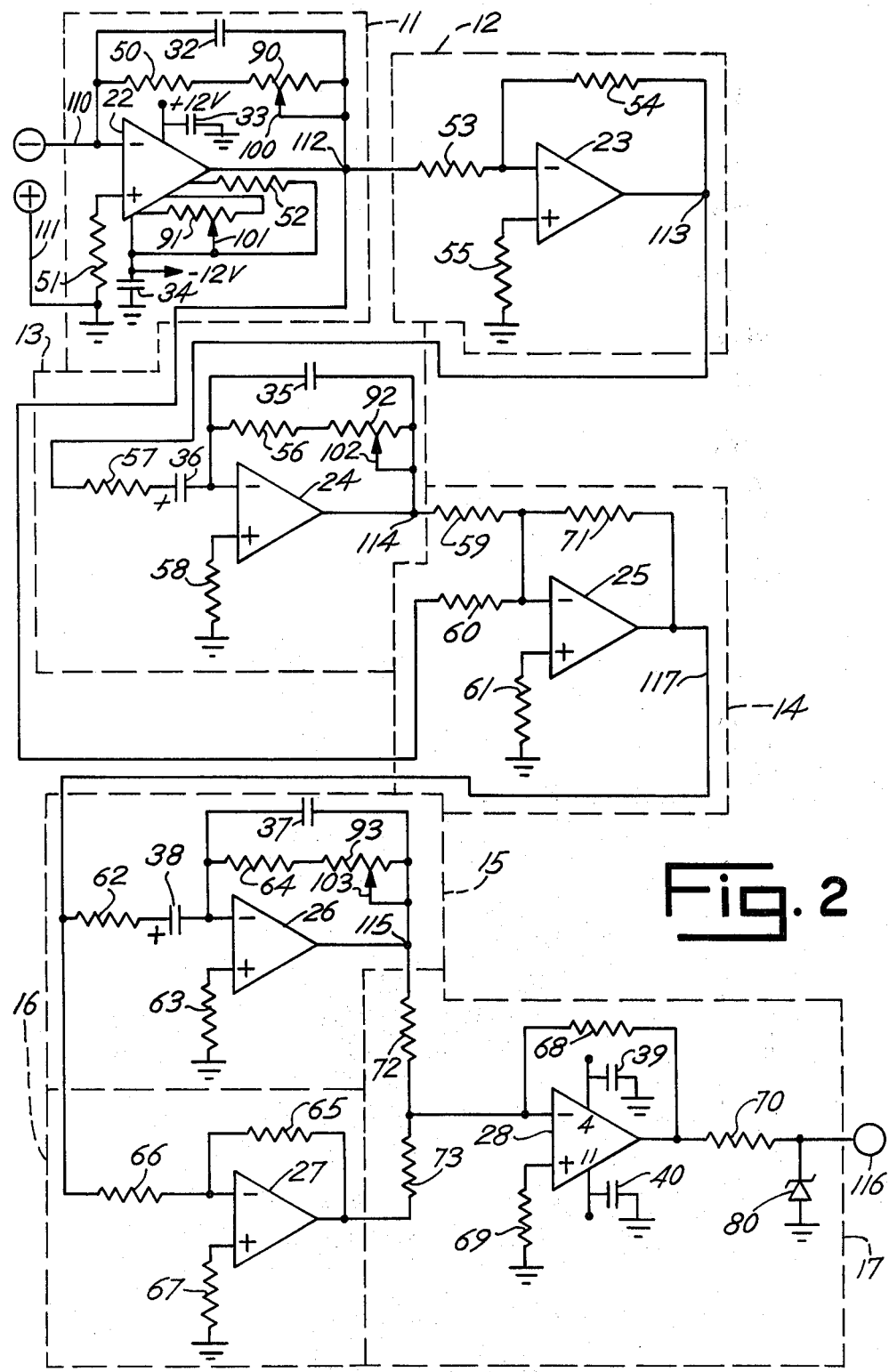
FIG. 2 is a detailed electrical schematic drawing of the circuitry shown in FIG. 1.

The details of circuit elements 11–17 are shown in FIG. 2, wherein the dotted line boxes around the circuit components correspond to the like numbered blocks shown in FIG. 1. The FIG. 2 circuitry includes operational amplifiers 22–28, capacitors 32–40, resistors 50–73, a zener diode 80, potentiometers 90–93 and corresponding wiper blades for the potentiometers 100–103, all connected as shown. The preferred values for the capacitors, resistors and potentiometers is shown in the following Table 1:

|  | Value |
| --- | --- |
| Capacitors |  |
| 32 | 220 PF |
| 33 | 0.1 MF |
| 34 | 0.1 MF |
| 35 | 1 MF |
| 36 | 10 MF |
| 37 | 1 MF |
| 38 | 10 MF |
| 39 | 0.1 MF |
| 40 | 0.1 MF |
| Resistors |  |
| 50 | 200K |
| 51 | 499 |
| 52 | 4.53M |
| 53 | 100K |
| 54 | 100K |
| 55 | 49.9K |
| 56 | 220K |
| 57 | 5.1K |
| 58 | 270K |
| 59 | 20K |
| 60 | 20K |
| 61 | 6.8K |
| 62 | 5.1K |
| 63 | 82K |
| 64 | 56K |
| 65 | 20K |
| 66 | 20K |
| 67 | 10K |

-continued

| | Value |
|---|---|
| 68 | 20K |
| 69 | 6.8K |
| 70 | 470 |
| 71 | 20K |
| 72 | 20K |
| 73 | 20K |
| Potentiometers | |
| 90 | 500K |
| 91 | 100K |
| 92 | 100K |
| 93 | 50K |

In the foregoing table, the notation PF mean picofarads and MF means microfarads. Resistor and potentiometer values are given in ohms, wherein K means a multiple of 1000 and M means a multiple of one million.

Referring to FIG. 2, the circuitry operates as follows. The outputs of sensor 10 are connected through conductors 110, 111 to the inverting and non-inverting inputs of operational amplifier 22, respectively. Operational amplifier 22 is a type LM 4250 which is programmed for low bias current of about 10 nano amperes. Oxygen sensor 10 produces current proportional to the partial pressure of oxygen in the incoming exhaust stream sample. This current is injected into the inverting terminal of amplifier 22 through conductor 110. The voltage produced at conductor 112 is proportional to the input current. Therefore, the voltage at conductor 112 is proportional to the partial pressure of oxygen in the exhaust stream sample. It decreases with the increase of oxygen content in the sample and vice versa. The current voltage gain of amplifier 22 is adjusted by potentiometer 90. Potentiometer 91 can be used to adjust the 0 offset of amplifier 22. Inverter 12 is simply an inverting amplifier with a gain of 1.

Differentiator 13 produces a signal proportional to the first derivative of the voltage produced on conductor 113. Differentiator 13 includes a three pole filter with pole frequencies $f_{c1}$, $f_{h1}$, $f_{h2}$ which equals 0.06 Hz., 0.6 Hz and 3.2 Hz, respectively. Pole frequency $f_{c1}$ is determined by the values of capacitor 36, resistor 56 and potentiometer 92; pole frequency $f_{h1}$ is determined by the values of capacitor 35, resistor 56 and potentiometer 92; and pole frequency $f_{h2}$ is determined by the values of capacitor 36 and resistor 57. Use of three pole filtering action in the differentiator is an important feature which enables the value of the oxygen of a sample stream to be predicted with a high degree of accuracy and at an early point in time.

Summer 14 algebraically adds at least a portion of the values of the voltages produced at conductors 112 and 114. The proportion of the voltages which are added by circuit 14 are determined by the values of resistors 59, 60 and 71.

Differentiator 15 is essentially identical to differentiator 13 except for the difference in component values. Differentiator 15 also includes three pole filtering action in which $f_{c2}=0.2$ Hz., $f_{h3}=2$ Hz., and $f_{h4}=3.2$ Hz. These pole frequencies are determined by the same relative components as those shown in differentiator 13. That is pole frequency $f_{c2}$ is determined by the values of resistor 64, potentiometer 93 and capacitor 38; pole frequency $f_{h3}$ is determined by the values of capacitor 37, resistor 64 and potentiometer 93; and pole frequency $f_{h4}$ is determined by the values of resistor 62 and capacitor 38.

With respect to both differentiators 13 and 15 the $f_c$ pole is the cut off frequency below which the signal is attenuated at 6 db's per octave; the $f_{h1}$ and $f_{h3}$ poles are the cut off frequencies above which the signal is attenuated at 6 db's per octave; and the $f_{h2}$ and $f_{h4}$ poles are the cut off frequencies above which the signal is attenuated at 12 db's per octave.

Inverter 16, like inverter 12, is merely an inverting amplifier with a gain of 1.

Summer 17 is essentially like summer 14.

The output signal produced at the output of summer 17 on conductor 116 takes the form:
$V+G1V'+G2V''$ where V equals the voltage on conductor 113, G1 and G2 are constants of proportionality, and V' and V'' are the first and second derivatives of V, respectively. This equation is derived as follows:

$$\begin{aligned}(V + K_1V') + K_2(V + K_1V')' &= \text{voltage on conductor 116} \\ &= V + K_1V' + K_2V' + K_1K_2V'' \\ &= V + (K_1 + K_2)V' + K_1K_2V'' \\ &= V + G1V' + G2V''\end{aligned}$$

In the foregoing equations, V equals the voltage on conductor 113 which is a function of time v(t). $K_1$ and $K_2$ are constants of proportionality, V' and V'' are the first and second derivatives of V, $-K_1V'$ is the output of differentiator 13 and $-K_2(V+K_1V')$ is the output of differentiator 15.

Figure 3:
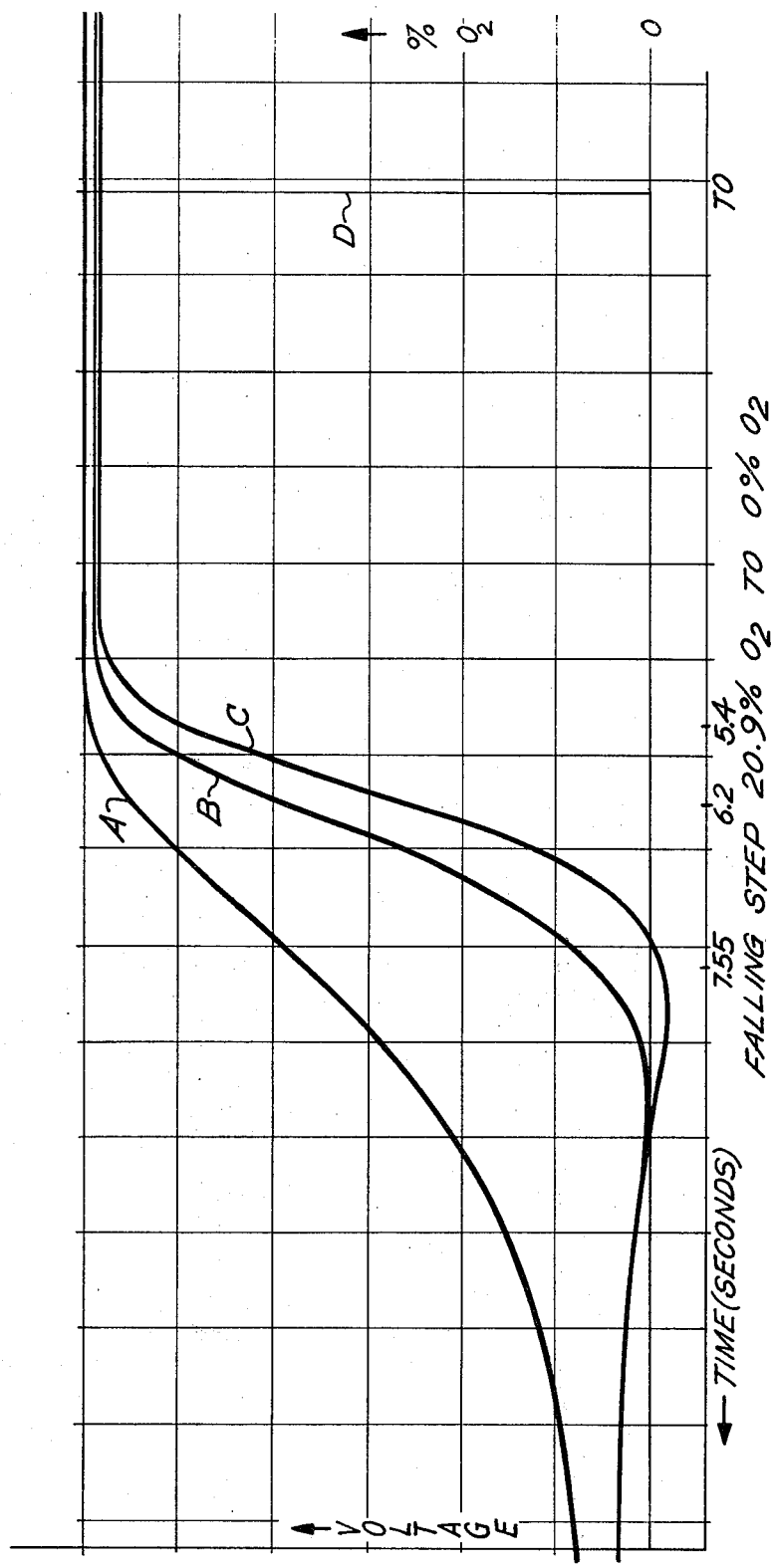
FIG. 3 is a graph showing three signals generated by the apparatus shown in FIG. 2 for the condition in which oxygen rapidly decreases in a step function from 20.9 percent to 0 percent.

FIG. 3 illustrates the voltages generated by the foregoing circuitry in response to a decreasing step function change in oxygen from 20.9 percent to 0 percent as a function of time. Curve A represents the voltage generated on conductor 113; curve B represents the voltage generated on conductor 117 and curve C represents the voltage generated on conductor 116; and curve D represents the step function change in oxygen at time T0.

Figure 4:
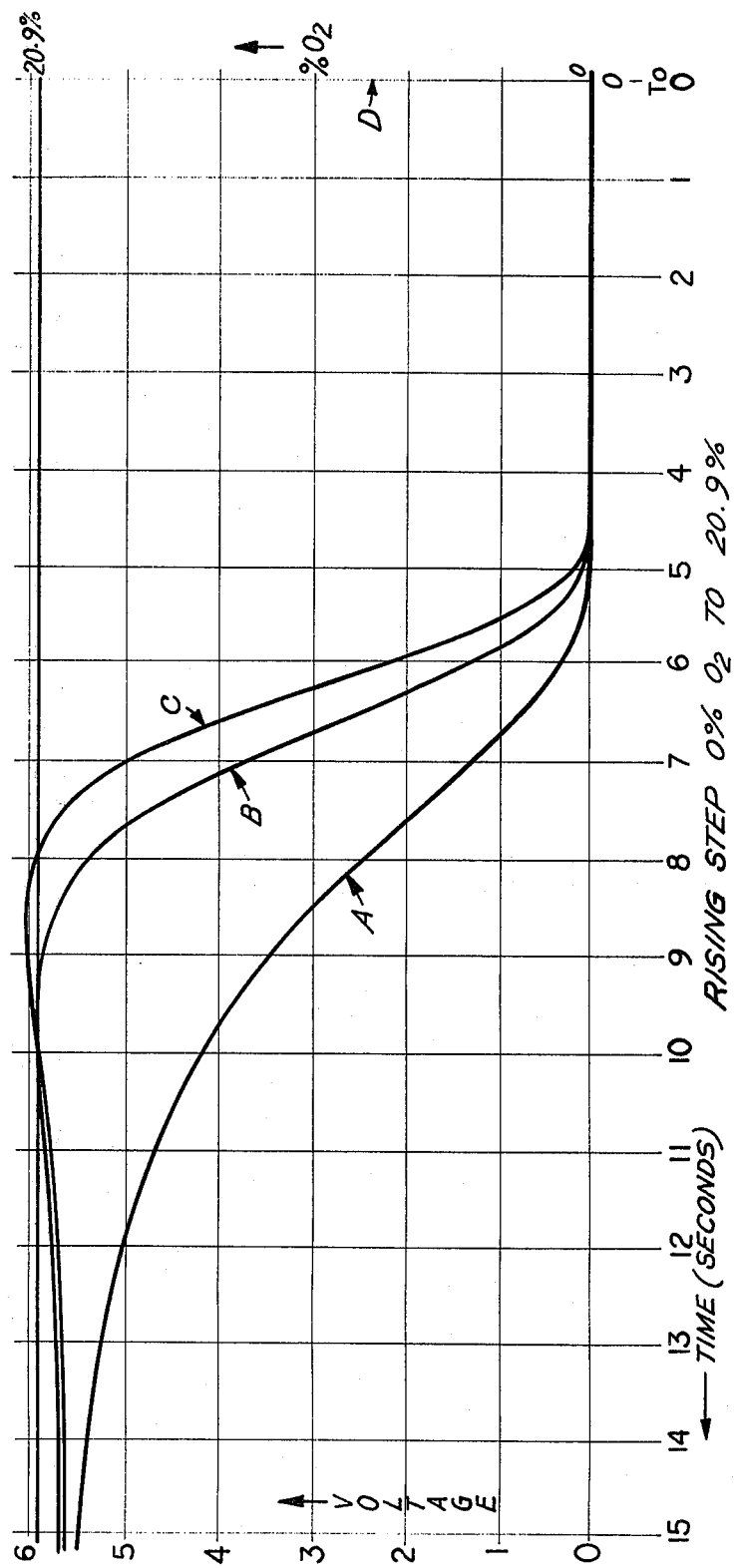
FIG. 4 is a graph showing three signals generated by the circuitry shown in FIG. 2 for the condition in which oxygen rapidly rises in a step function from 0 percent to 20.9 percent.

FIG. 4 represents the voltages generated by the foregoing circuitry in response to a rising step function change in oxygen from 0 percent to 20.9 percent as a function of time. Curves A, B and C represent the voltages on the same conductors as curves A, B and C shown in FIG. 3. Curve D represents the step function change in oxygen at time T0.

As illustrated by the curves in FIGS. 3 and 4, use of the foregoing circuitry enables the anticipation of the concentration of oxygen in the exhaust sample long before the time required by the use of an oxygen sensor alone. This is an important advantage which enables oxygen, hydrocarbons and carbon monoxide to be displayed at approximately the same time on meters or a cathode ray tube.

Although the best mode of the invention has been described in the specification, those skilled in the art will recognize that the advantages of the invention can be obtained by altering and modifying the best mode within the spirit and scope of the appended claims.

What is claimed is:

1. In a system for analyzing the concentration of a predetermined gas by use of a sensor means for generating a sensor signal having a sensor value proportional to the partial pressure of the predetermined gas after a predetermined time period, improved apparatus for anticipating the amount of the concentration before the time period expires comprising:

signal processing means for generating a resulting signal proportional to the sum of the sensor value, another value proportional to the first derivative of the sensor value and a third value proportional to the second derivative of the sensor value, the signal processing means further comprising filter means for attenuating at a first rate signals having a frequency below a first cut off frequency, for attenuating at a second rate signals having a frequency above a second cut off frequency and for attenuating at a third rate signals having a frequency above a third cut off frequency greater than the second cut off frequency, and display means for displaying information related to the concentration based on the resulting signal.

2. In a system for analyzing the concentration of a predetermined gas by use of a sensor means for generating a sensor signal having a sensor value proportional to the partial pressure of the predetermined gas after a predetermined time period, improved apparatus for anticipating the amount of the concentration before the time period expires comprising:

signal processing means for generating a resulting signal proportional to the sum of the sensor value, another value proportional to the first derivative of the sensor value and a third value proportional to the second derivative of the sensor value, said signal processing means comprising:
- (a) first differentiating means for generating a first rate signal proportional to the rate of change of the sensor signal;
- (b) first summing means for generating a first summed signal proportional to the sum of at least a portion of the sensor signal and at least a portion of the first rate signal;
- (c) second differentiating means for generating a second rate signal proportional to the rate of change of the first summed signal;
- (d) second summing means for generating said resulting signal proportional to the sum of at least a portion of the first summed signal and at least a portion of the second rate signal; and
- (e) filter means for attenuating at a first rate signals having a frequency below a first cut off frequency, for attenuating at a second rate signals having a frequency above a second cut off frequency and for attenuating at a third rate signals having a frequency above a third cut off frequency greater than the second cut off frequency; and display means for displaying information related to the concentration based on the resulting signal.

3. Apparatus, as claimed in claim 1 or 2, wherein the predetermined gas is oxygen.

4. In a process for analyzing the concentration of a predetermined gas by use of a sensor means for generating a sensor signal having a sensor value proportional to the partial pressure of the predetermined gas after a predetermined time period, an improved method for anticipating the amount of the concentration before the time period expires comprising the steps of:

generating a resulting signal proportional to the sum of the sensor value, another value proportional to the first derivative of the sensor value and a third value proportional to the second derivative of the sensor value, the step of generating further comprising attenuating at a first rate signals having a frequency below a first cut off frequency, attenuating at a second rate signals having a frequency above a second cut off frequency and attenuating at a third rate signals having a frequency above a third cut off frequency greater than the second cut off frequency; and displaying information related to the concentration based on the resulting signal.

5. In a process of analyzing the concentration of a predetermined gas by use of a sensor means for generating a sensor signal having a sensor value proportional to the partial pressure of the predetermined gas after a predetermined time period, an improved method for anticipating the amount of the concentration before the time period expires comprising the steps of:

generating a resulting signal proportional to the sum of the sensor value, another value proportional to the first derivative of the sensor value and a third value proportional to the second derivative of the sensor value, said step of generating comprising:
- (a) generating a first rate signal proportional to the rate of change of the sensor signal;
- (b) generating a first summed signal proportional to the sum of at least a portion of the sensor signal and at least a portion of the first rate signal;
- (c) generating a second rate signal proportional to the rate of change of the first summed signal;
- (d) generating said resulting signal proportional to the sum of at least a portion of the first summed signal and at least a portion of the second rate signal;
- (e) attenuating at a first rate signals having a frequency below a first cut off frequency;
- (f) attenuating at a second rate signals having a frequency above a second cut off frequency; and
- (g) attenuating at a third rate signals having a frequency above a third cut off frequency greater than the second cut off frequency; and displaying information related to the concentration based on the resulting signal.

6. A process, as claimed in claim 4 or 5, wherein the predetermined gas is oxygen.

* * * * *